US007427521B2

(12) United States Patent
Bischoff et al.

(10) Patent No.: US 7,427,521 B2
(45) Date of Patent: Sep. 23, 2008

(54) GENERATING SIMULATED DIFFRACTION SIGNALS FOR TWO-DIMENSIONAL STRUCTURES

(75) Inventors: Joerg Bischoff, Ilmenau (DE); Xinhui Niu, Los Altos, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 1116 days.

(21) Appl. No.: 10/274,252

(22) Filed: Oct. 17, 2002

(65) Prior Publication Data

US 2004/0078173 A1    Apr. 22, 2004

(51) Int. Cl.
*H01L 21/66* (2006.01)
(52) U.S. Cl. ........................................ 438/16
(58) Field of Classification Search ........ 702/189
See application file for complete search history.

(56) References Cited

U.S. PATENT DOCUMENTS 6,720,575 B2    4/2004    Yamazaki et al.
6,721,691 B2 *  4/2004    Bao et al. ............... 702/189
6,734,982 B2    5/2004    Banet et al.
6,785,638 B2 *  8/2004    Niu et al. ............... 702/189

OTHER PUBLICATIONS

International Search Report mailed on Oct. 13, 2004, for PCT patent application No. PCT/US03/32779 filed on Nov. 20, 2003, 2 pages.

* cited by examiner

*Primary Examiner*—Scott B. Geyer
*Assistant Examiner*—Andre' Stevenson
(74) *Attorney, Agent, or Firm*—Morrison & Foerster LLP

(57) ABSTRACT

One or more simulated diffraction signals for use in determining the profile of a structure formed on a semiconductor wafer can be generated, where the profile varies in more than one dimension. Intermediate calculations are generated for variations in a hypothetical profile of the structure in a first dimension and a second dimension, where each intermediate calculation corresponds to a portion of the hypothetical profile of the structure. The generated intermediate calculations are then stored and used in generating one or more simulated diffraction signals for one or more hypothetical profiles of the structure.

43 Claims, 16 Drawing Sheets

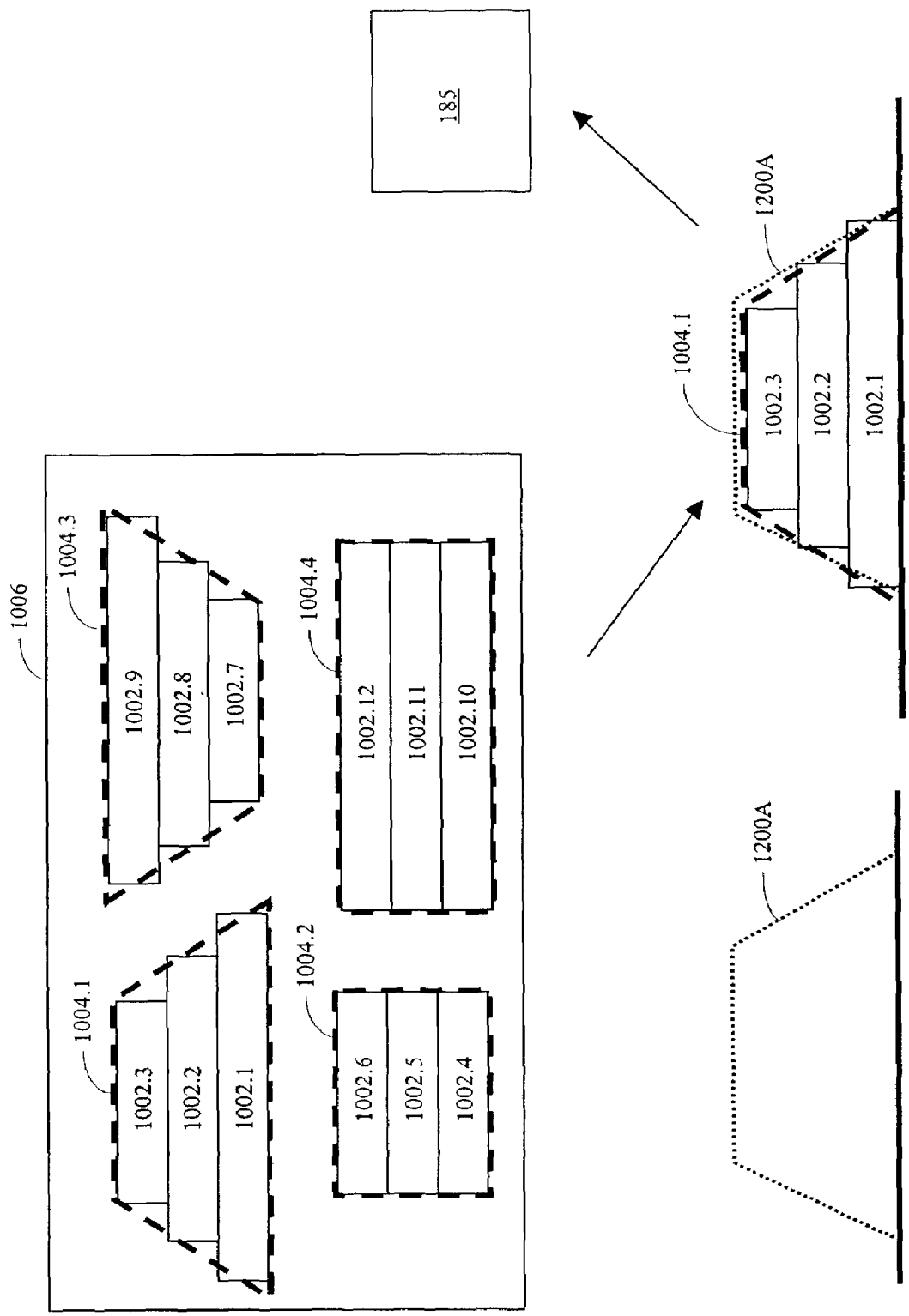

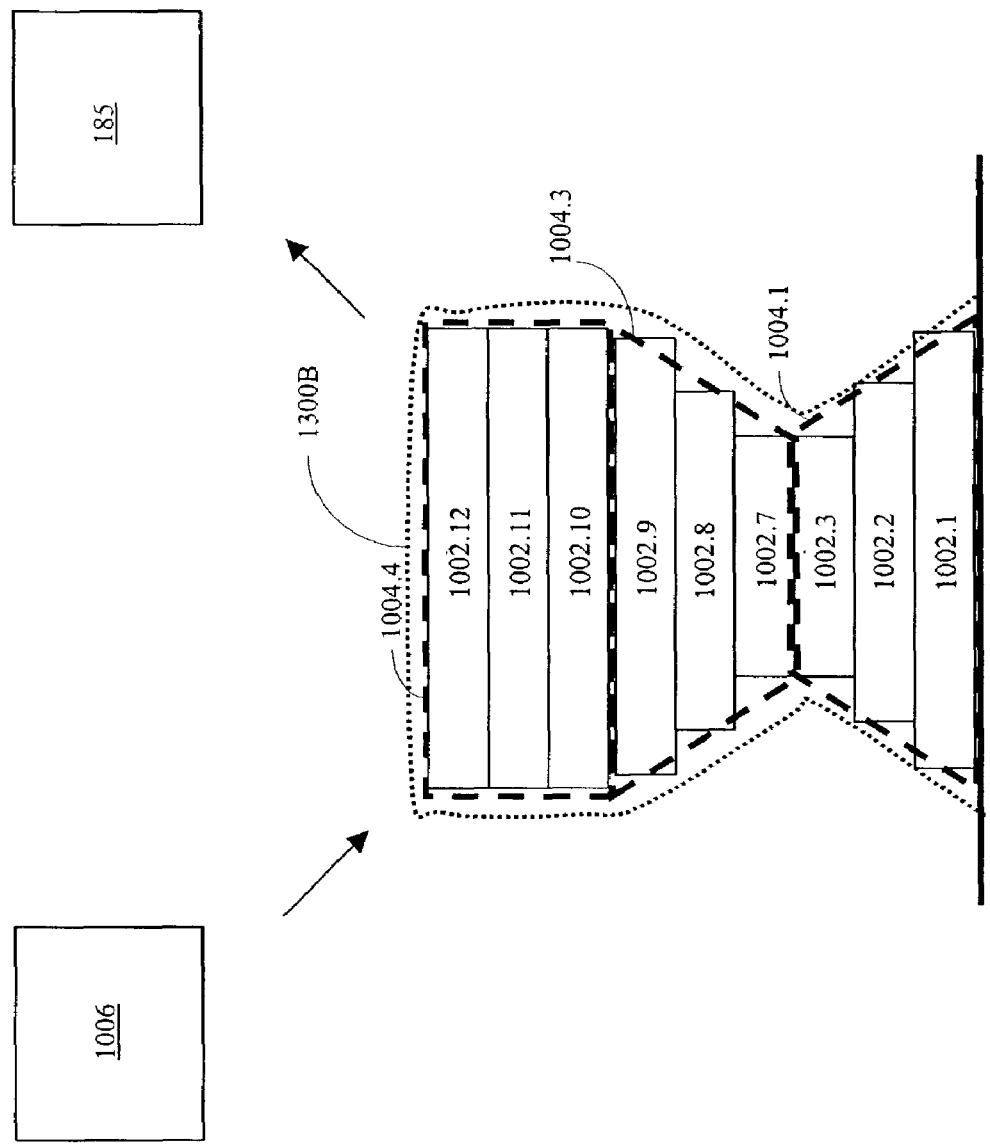

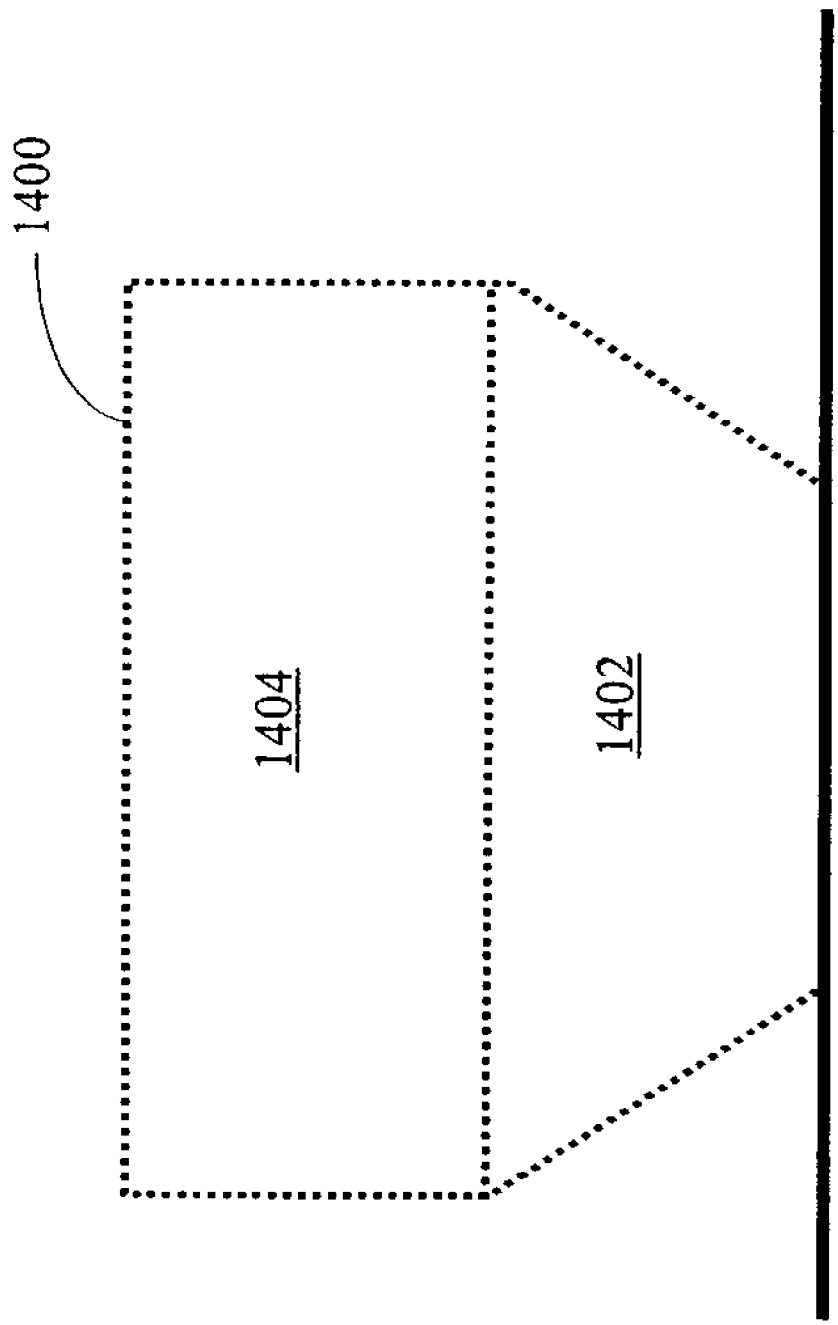

GENERATING SIMULATED DIFFRACTION SIGNALS FOR TWO-DIMENSIONAL STRUCTURES

BACKGROUND

1. Field of the Invention

The present invention relates to wafer metrology, and more particularly to generating simulated diffraction signals for use in optical metrology.

2. Related Art

Optical metrology can be utilized to determine the profile of structures formed on semiconductor wafers. In general optical metrology involves directing an incident beam at a structure and measuring the resulting diffraction beam. The characteristics of the measured diffraction beam (i.e., a measured diffraction signal) is typically compared to pre-determined diffraction signals (i.e., simulated diffraction signals) that are associated with known profiles. When a match is made between the measured diffraction signal and one of the simulated diffraction signals, then the profile associated with the matching simulated diffraction signal is presumed to represent the profile of the structure.

In general, the process of generating a simulated diffraction signal involves performing a large number of complex calculations, which can be time and computationally intensive. The number and complexity of the calculations increases for structures having profiles that vary in more than one dimension.

SUMMARY

In one exemplary embodiment, one or more simulated diffraction signals for use in determining the profile of a structure formed on a semiconductor wafer are generated, where the profile varies in more than one dimension. Intermediate calculations are generated for variations in a hypothetical profile of the structure in a first dimension and a second dimension, where each intermediate calculation corresponds to a portion of the hypothetical profile of the structure. The generated intermediate calculations are then stored and used in generating one or more simulated diffraction signals for one or more hypothetical profiles of the structure.

DESCRIPTION OF DRAWING FIGURES

The present invention can be best understood by reference to the following description taken in conjunction with the accompanying drawing figures, in which like parts may be referred to by like numerals:

FIGS. 12A and 12B depict an exemplary process of generating simulated diffraction signals for a hypothetical profile of a structure;

FIGS. 13A and 13B depict another exemplary process of generating simulated diffraction signals for a hypothetical profile of a structure;

FIGS. 14A and 14B depict still another exemplary process of generating simulated diffraction signals for a hypothetical profile of a structure;

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology

Figure 1:
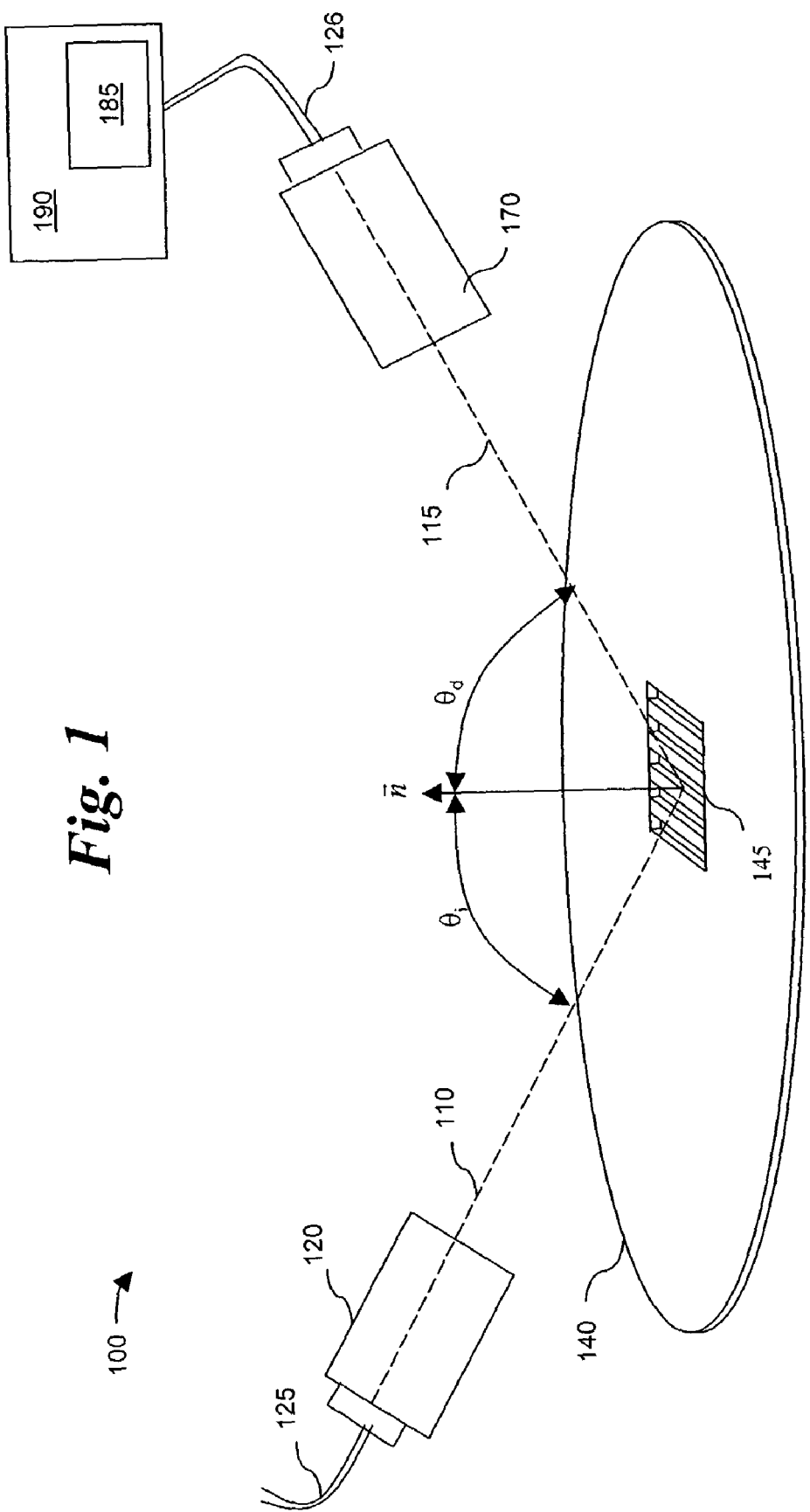
FIG. 1 depicts an exemplary optical-metrology system.

In one exemplary embodiment, optical-metrology can be utilized to determine the profile of a structure formed on a semiconductor wafer. As depicted in FIG. 1, an optical-metrology system 100 can include an electromagnetic source 120, such as an ellipsometer, reflectometer, and the like. A structure 145 is illuminated by an incident beam 110 from electromagnetic source 120. Incident beam 110 is directed onto structure 145 at an angle of incidence $\theta_i$ with respect to normal $\vec{n}$ of structure 145. Diffraction beam 115 leaves at an angle of $\theta_d$ with respect to normal $\vec{n}$.

As depicted in FIG. 1, diffraction beam 115 is received by detector 170. When electromagnetic source 120 is an ellipsometer, the relative magnitude ($\Psi$) and the phase ($\Delta$) of diffraction beam 115 are received and detected. When electromagnetic source 120 is a reflectometer, the relative intensity of diffraction beam 115 is received and detected.

To determine the profile of structure 145, optical-metrology system 100 includes a processing module 190, which converts diffraction beam 115 received by detector 170 into a diffraction signal (i.e., a measured diffraction signal). As described below, the profile of structure 145 can then be determined using either a library-based process or a regression-based process.

2. Library-based Process of Determining Profile of Structure

In a library-based process of determining the profile of a structure, the measured diffraction signal is compared to a library of simulated diffraction signals. More specifically, each simulated diffraction signal in the library is associated with a hypothetical profile of the structure. When a match is made between the measured diffraction signal and one of the simulated diffraction signals in the library, such as within a preset criteria, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, after obtaining a measured diffraction signal, processing module 190 compares the measured diffraction signal to simulated diffraction signals stored in a library 185. Library 185 includes simulated diffraction signals that are associated with hypothetical profiles of structure 145. More particularly, in one exemplary embodiment, library 185 includes pairings of simulated diffraction signals and hypothetical profiles of structure 145. The simulated diffraction signal in each pairing includes hypothetically generated reflectances that characterize the predicted behavior of diffraction beam 115 assuming that the profile of the structure 145 is that of the hypothetical profile in the simulated diffraction signal and hypothetical profile pairing.

The set of hypothetical profiles stored in library 185 can be generated by characterizing a hypothetical profile using a set of parameters, then varying the set of parameters to generate hypothetical profiles of varying shapes and dimensions. The process of characterizing a profile using a set of parameters can be referred to as parameterizing.

Figure 2E:
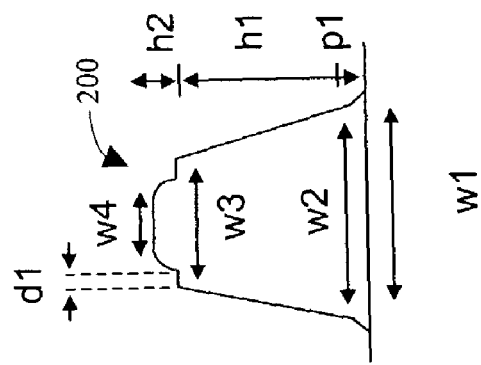
FIGS. 2A-2E depict various hypothetical profiles of a structure.
Figure 2C:
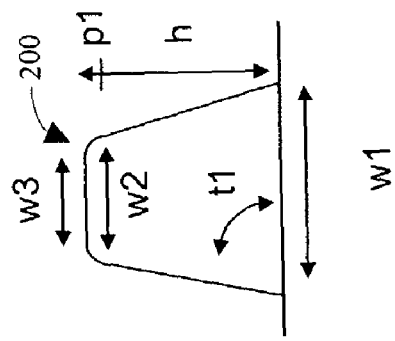
Figure 2D:
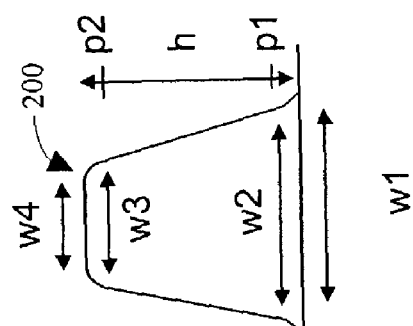
Figure 2A:
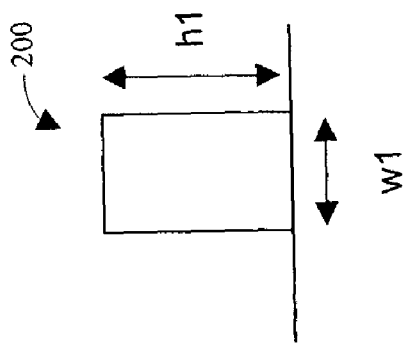
Figure 2B:
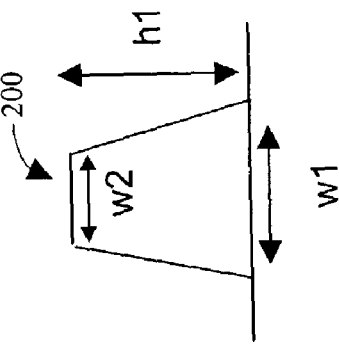

For example, as depicted in FIG. 2A, assume that hypothetical profile 200 can be characterized by parameters h1 and w1 that define its height and width, respectively. As depicted in FIGS. 2B to 2E, additional shapes and features of hypothetical profile 200 can be characterized by increasing the number of parameters. For example, as depicted in FIG. 2B, hypothetical profile 200 can be characterized by parameters h1, w1, and w2 that define its height, bottom width, and top width, respectively. Note that the width of hypothetical profile 200 can be referred to as the critical dimension (CD). For example, in FIG. 2B, parameter w1 and w2 can be described as defining the bottom CD and top CD, respectively, of hypothetical profile 200.

As described above, the set of hypothetical profiles stored in library 185 (FIG. 1) can be generated by varying the parameters that characterize the hypothetical profile. For example, with reference to FIG. 2B, by varying parameters h1, w1, and w2, hypothetical profiles of varying shapes and dimensions can be generated. Note that one, two, or all three parameters can be varied relative to one another.

With reference again to FIG. 1, the number of hypothetical profiles and corresponding simulated diffraction signals in the set of hypothetical profiles and simulated diffraction signals stored in library 185 (i.e., the resolution and/or range of library 185) depends, in part, on the range over which the set of parameters and the increment at which the set of parameters are varied. In one exemplary embodiment, the hypothetical profiles and the simulated diffraction signals stored in library 185 are generated prior to obtaining a measured diffraction signal from an actual structure. Thus, the range and increment (i.e., the range and/or resolution) used in generating library 185 can be selected based on familiarity with the fabrication process for a structure and what the range of variance is likely to be. The range and/or resolution of library 185 can also be selected based on empirical measures, such as measurements using AFM, X-SEM, and the like.

For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety.

3. Regression-based Process of Determining Profile of Structure

In a regression-based process of determining the profile of a structure, the measured diffraction signal is compared to a simulated diffraction signal (i.e., a trial spectrum signal). The simulated diffraction signal is generated prior to the comparison using a set of parameters (i.e., trial parameters) for a hypothetical profile (i.e., a hypothetical profile). If the measured diffraction signal and the simulated diffraction signal do not match, such as within a preset criteria, another simulated diffraction signal is generated using another set of parameters for another hypothetical profile, then the measure-diffraction signal and the newly generated simulated diffraction signal are compared. When the measured diffraction signal and the simulated diffraction signal match, such as within a preset criteria, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, processing module 190 can generate a simulated diffraction signal for a hypothetical profile, then compare the measured diffraction signal to the simulated diffraction signal. As described above, if the measured diffraction signal and the simulated diffraction signal do not match, such as within a preset criteria, then processing module 190 can iteratively generate another simulated diffraction signal for another hypothetical profile. In one exemplary embodiment, the subsequently generated simulated diffraction signal can be generated using an optimization algorithm, such as global optimization techniques, which includes simulated annealing, and local optimization techniques, which includes steepest descent algorithm.

In one exemplary embodiment, the simulated diffraction signals and hypothetical profiles can be stored in a library 185 (i.e., a dynamic library). The simulated diffraction signals and hypothetical profiles stored in library 185 can then be subsequently used in matching the measured diffraction signal.

For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

4. Rigorous Coupled Wave Analsysis

As described above, simulated diffraction signals are generated to be compared to measured diffraction signals. As will be described below, in one exemplary embodiment, simulated diffraction signals can be generated by applying Maxwell's equations and using a numerical analysis technique to solve Maxwell's equations. More particularly, in the exemplary embodiment described below, rigorous coupled-wave analysis (RCWA) is used. It should be noted, however, that various numerical analysis techniques, including variations of RCWA, can be used.

In general, RCWA involves dividing a profile into a number of sections, slices, or slabs (hereafter simply referred to as sections). For each section of the profile, a system of coupled differential equations generated using a Fourier expansion of Maxwell's equations (i.e., the components of the electromagnetic field and permittivity ($\epsilon$)). The system of differential equations is then solved using a diagonalization procedure that involves eigenvalue and eigenvector decomposition (i.e., Eigen-decomposition) of the characteristic matrix of the related differential equation system. Finally, the solutions for each section of the profile are coupled using a recursive-coupling schema, such as a scattering matrix approach. For a description of a scattering matrix approach, see Lifeng Li, "Formulation and comparison of two recursive matrix algorithms for modeling layered diffraction gratings," J. Opt. Soc. Am. A13, pp 1024-1035(1996), which is incorporated herein by reference in its entirety. For a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

In RCWA, the Fourier expansion of Maxwell's equations is obtained by applying the Laurent's rule or the inverse rule. When RCWA is performed on a structure having a profile that varies in at least one dimension/direction, the rate of convergence can be increased by appropriately selecting between the Laurent's rule and the inverse rule. More specifically, when the two factors of a product between permittivity ($\epsilon$) and an electromagnetic field (E) have no concurrent jump discontinuities, then the Laurent's rule is applied. When the factors (i.e., the product between the permittivity ($\epsilon$) and the electromagnetic filed (E)) have only pairwise complimentary jump discontinuities, the inverse rule is applied. For a more detailed description, see Lifeng Li, "Use of Fourier series in the analysis of discontinuous periodic structures," J. Opt. Soc. Am. A13, pp 1870-1876 (September, 1996), which is incorporated herein by reference in its entirety.

Figure 3:
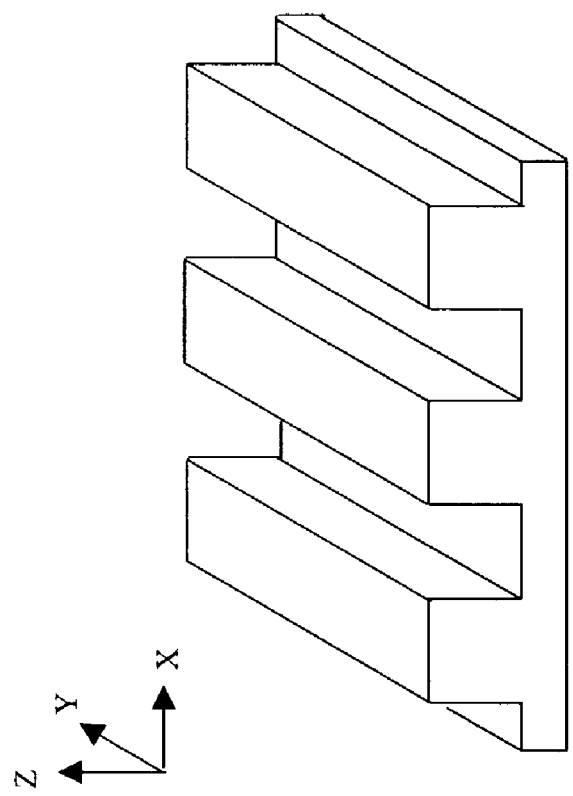
FIG. 3 depicts an exemplary one-dimension structure.

For a structure having a profile that varies in one dimension (referred to herein as a one-dimension structure), the Fourier expansion is performed only in one direction, and the selection between applying the Laurent's rule and the inverse rule is also made only in one direction. For example, a periodic grating depicted in FIG. 3 has a profile that varies in one dimension (i.e., the x-direction), and is assumed to be substantially uniform or continuous in the y-direction. Thus, the Fourier expansion for the periodic grating depicted in FIG. 3 is performed only in the x direction, and the selection between applying the Laurent's rule and the inverse rule is also made only in the x direction.

Figure 4:
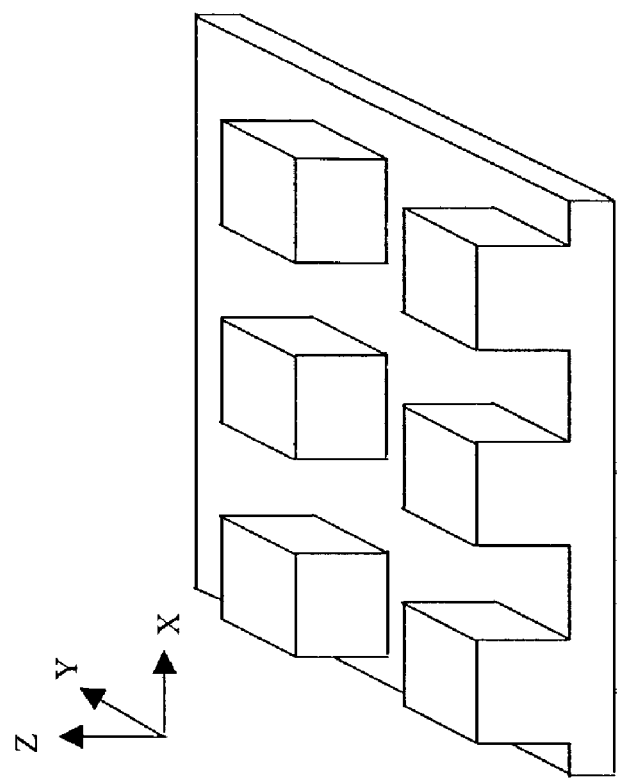
FIG. 4 depicts an exemplary two-dimension structure.

However, for a structure having a profile that varies in two or more dimensions (referred to herein as a two-dimension structure), the Fourier expansion is performed in two directions, and the selection between applying the Laurent's rule and the inverse rule is also made in two directions. For example, a periodic grating depicted in FIG. 4 has a profile that varies in two dimensions (i.e., the x-direction and the y-direction). Thus, the Fourier expansion for the periodic grating depicted in FIG. 4 is performed in the x direction and the y-direction, and the selection between applying the Laurent's rule and the inverse rule is also made in the x direction and the y direction.

Figure 6:
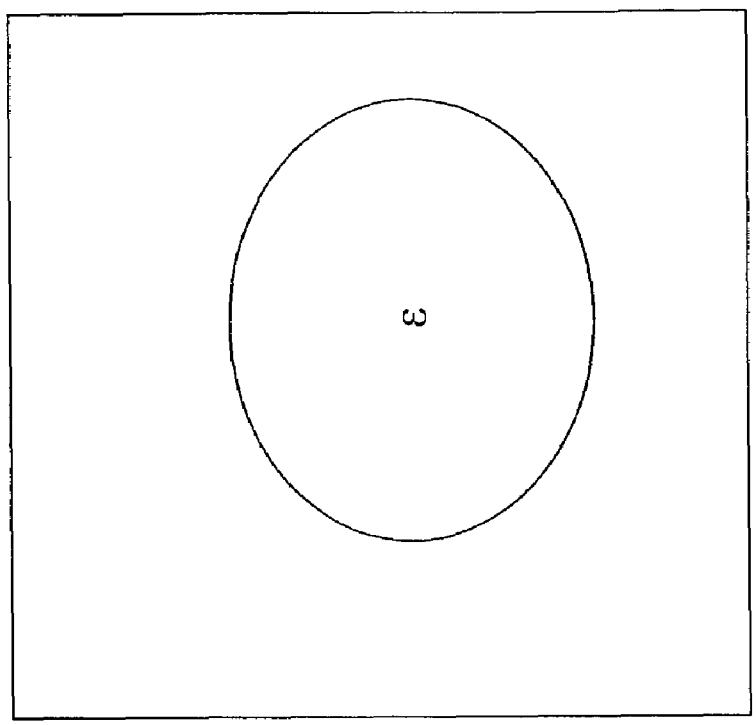
FIG. 6 is a top view of another exemplary structure.
Figure 5:
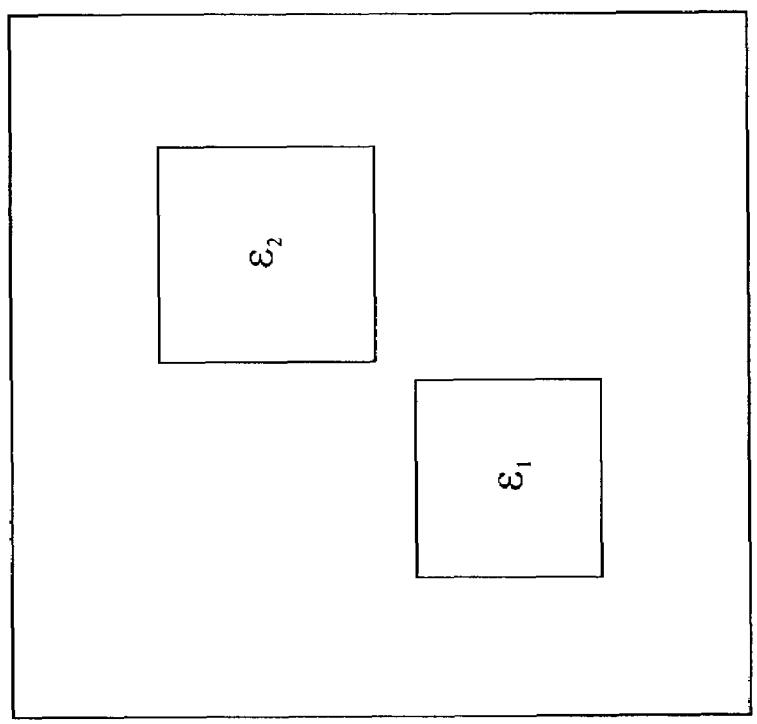
FIG. 5 is a top view of an exemplary structure.

Additionally, for a one-dimension structure, Fourier expansion can be performed using an analytic Fourier transformation (e.g., a sin(v)/v function). However, for a two-dimension structure, Fourier expansion can be performed using an analytic Fourier transformation only when the structure has a rectangular patched pattern, such as that depicted in FIG. 5. Thus, for all other cases, such as when the structure has a non-rectangular pattern (an example of which is depicted in FIG. 6), a numerical Fourier transformation (e.g., by means of a Fast Fourier Transformation) is performed.

Figure 7:
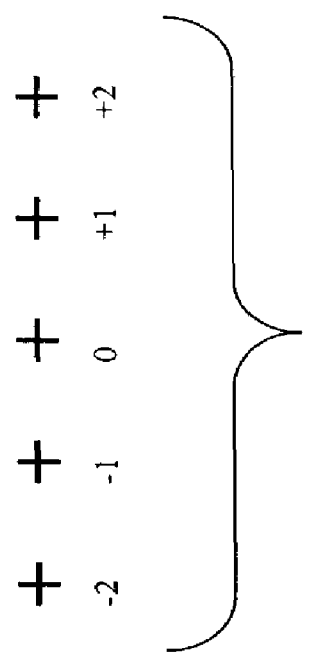
FIG. 7 depicts a chain of harmonic orders.

In RCWA, all of the harmonic orders are placed in relation to each other. For a one-dimension structure, this process is straightforward because the harmonic orders can be ordered in a chain. For example, as depicted in FIG. 7, harmonic orders ranging from −2 to +2 can be ordered in a simple chain from −2 to +2. Thus, each harmonic order can be related to each other on a one-to-one basis.

Figure 8:
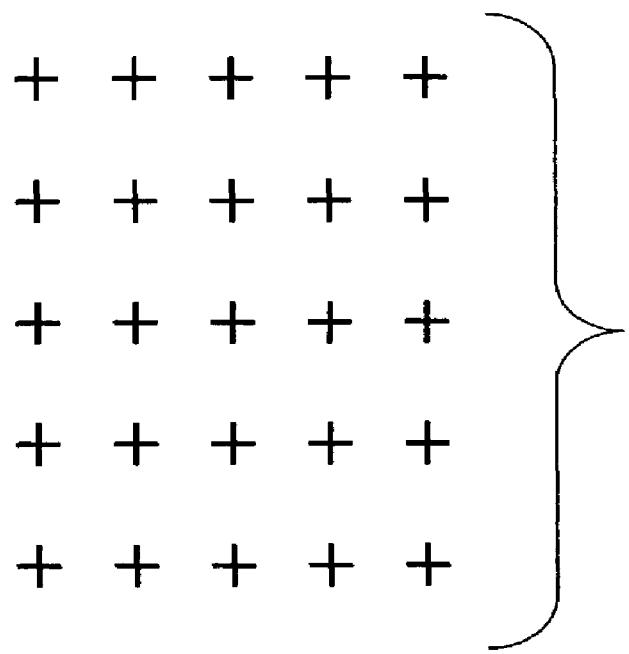
FIG. 8 depicts an array of harmonic orders.

In contrast, for a two-dimension structure, as depicted in FIG. 8, the diffraction orders occur in an array. Thus, in order to relate a pair of orders to another pair of orders, the array of diffraction orders is projected into one dimension. Therefore, each pair of orders are sorted and the algorithm is organized correspondingly to ensure the correct orders are used.

For example, in one exemplary embodiment, in order to compute the modes outside and inside a homogeneous section (i.e., Rayleigh modes for a section) and to formulate the differential equations for the electromagnetic field, the dispersion relation is defined as follows:

$$\gamma_{m,n} = \sqrt{k^2 \cdot \varepsilon - \alpha^2 - \beta^2}$$

$$\alpha = \alpha_0 + m \cdot \frac{\lambda}{p_x} \text{ and } \beta = \beta_0 + n \cdot \frac{\lambda}{p_y}$$

Here, m and n are the number of the two-dimensional diffraction order related to x and y directions, respectively; $p_x$ and $p_y$ are the respective periods; k is the wave number ($2\pi/\lambda$); and $\epsilon$ is the permittivity ($=n^2$). In the superstrate (i.e., the medium from which the structure is illuminated), $\epsilon$ is supposed to be a real number, i.e., there is no absorption. If $\alpha^2+\beta^2$ is less than $k^2$, then $\gamma$ is purely a real number, which means physically that the respective mode is propagating. However, if $\alpha^2+\beta^2$ is greater than $k^2$, $\gamma$ is purely an imaginary number, which means that the respective mode is evanescent, i.e., exponentially decaying. Therefore, the orders can be sorted related to the value of the term $\alpha^2+\beta^2$ starting with the least values. In this way, it is ensured that the $\gamma_{m,n}$ (with m,n indicating the two-dimensional order) and thus the orders m,n itself are sorted by the degree of their evanescence.

Additionally, as described above, the eigenvalues and eigenvectors can be obtained from the Eigen-decomposition. The corresponding modes (inside a periodic section) are called Bragg-modes. Depending on whether a first- or a second-order differential equation was solved, the eigenvalues can be taken directly or the square root is computed. In the latter case, an appropriate solution of the square root can be obtained by enforcing that the imaginary part of the square root is positive. Then, the eigenvalues and thus the orders are sorted by the imaginary part starting with the least value, and the eigenvectors are sorted correspondingly.

For the sake of example, a checkerboard grating is depicted in FIG. 4 as a two-dimension structure. It should be recognized, however, that a two-dimension structure can include various structures having profiles that vary in more than one dimension, such as contact holes, posts, and the like.

5. Caching and Retrieval of Eigensolutions

As described above, the process of generating a simulated diffraction signal can involve performing a large number of complex calculations. Additionally, as the complexity of the hypothetical profile increases, so does the number and complexity of the calculations needed to generate the simulated diffraction signal for the hypothetical profile.

As such, in one exemplary embodiment, a portion of the calculations performed in generating simulated diffraction signals can be stored as intermediate calculations prior to generating one or more simulated diffraction signals. As described above, in RCWA, the system of differential equations for each section of a profile is solved using, in part, Eigen-decomposition. Thus, in the present embodiment, the eigenvalues and eigenvectors (i.e., the eigensolutions) that are to be used in solving the system of differential equations for each section of the profile are calculated and stored prior to generating one or more simulated diffraction signals. The previously calculated and stored eigensolutions are retrieved when the system of differential equations are to be solved in generating one or more simulated diffraction signals.

Figure 9:
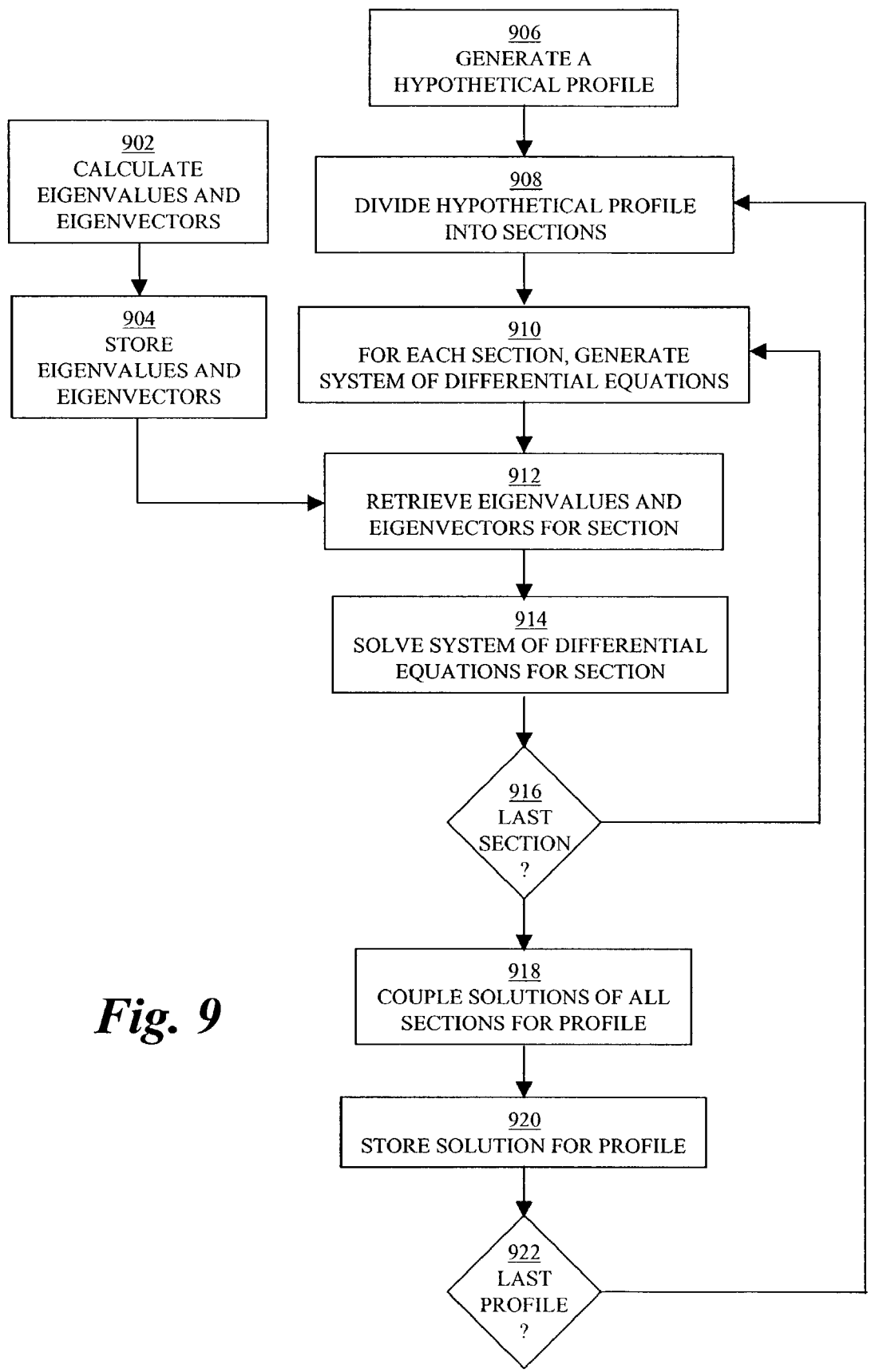
FIG. 9 depicts an exemplary process of generating simulated diffraction signals.

More particularly, with reference to FIG. 9, in the present exemplary embodiment, in step 902, prior to generating one or more simulated diffraction signals for one or more hypothetical profiles, a set of eigensolutions are calculated, which will be used in generating the one or more simulated diffraction signals for the one or more hypothetical profiles. Thus, the set of eigensolutions are calculated for the various geometries and/or materials that may be used in generating the one or more simulated diffraction signals for the one or more hypothetical profiles.

More specifically, as described above, in generating the one or more simulated diffraction signals for one or more hypothetical profiles, each hypothetical profile is divided into a number of sections, where the geometry of a particular section corresponds to the geometry of a particular portion of the hypothetical profile. Additionally, each hypothetical profile can be comprised of layers of different material. Thus, a particular section can correspond to the material in a particular portion of the hypothetical profile.

For example, a hypothetical profile can be divided into a number of rectangular sections, with each rectangular section having a different width that corresponds to the width of a particular portion of the hypothetical profile. Note that while the eigensolutions are sensitive to changes in width, meaning that rectangular sections of different width have different eigensolutions, they are not sensitive to changes in height, meaning that rectangular sections of different height have the same eigensolutions. Thus, when rectangular sections are used, a set of eigensolutions can be calculated for the various width of rectangular sections that may be used in generating the library.

Additionally, for the sake of example, assume that the hypothetical profile comprises a layer of oxide on top of a layer of resist. In this example, the hypothetical profile can be divided into at least two sections with the first section corresponding to the oxide layer and the second section corresponding to the resist layer. Thus, eigensolutions are calculated for the oxide layer and the resist layer. Also, assuming that rectangular sections are used, eigensolutions are calculated for rectangular sections of varying widths that are comprised of oxide, which will correspond to the first section of the hypothetical profiles, and rectangular sections of varying widths that are comprised of resist, which will correspond to the second section of the hypothetical profiles.

Furthermore, for the sake of clarity, the sections of a hypothetical profile have been depicted in two dimensions. It should be noted, however, that for a structure having a profile that varies in two or more dimensions (i.e., two-dimension structure), the sections can have more complex shapes and parameterizations.

For example, if rectangular sections are used, the rectangular sections can have widths in two dimensions (e.g., a width in a x-direction, a width in a y-direction, which may be orthogonal or not), one or more rounded corners, and the like. Additionally, if elliptical sections are used, such as for contact holes or posts, the elliptical sections can have diameters (e.g., a diameter in a x-direction, a diameter in a y-direction), a parameter that describes the deviation from an ellipse or a rectangle (e.g., an elliptical exponent that is equal to 2 for an ellipse and increases the more the ellipsoidal cross section shape approaches a rectangle), and the like.

It should be noted, however, that the sections can have various shapes of varying complexity. For example, the sections can include combinations of shapes, such as a combination of rectangular shapes.

In step 904, the set of calculated eigensolutions are stored. The set of calculated eigensolutions can be stored in memory, file, and the like. Additionally, the set of calculated eigensolutions can be indexed for ease of retrieval.

In one exemplary embodiment, in the manner described above, sets of calculated eigensolutions are generated and stored for varying geometry and/or material as well as varying wavelength or angle of incidence for use in generating one or more simulated diffraction signals based on the stored eigensolutions. In one particular exemplary embodiment, the sets of calculated eigensolutions are generated and stored in accordance with a nesting hierarchy, meaning that the eigensolutions are generated and stored in multiple nested iterations (i.e., loops) of one or more parameters (i.e., geometry, material, wavelength, angle of incidence, and the like).

For example, in a first loop, the geometry of the sections is varied. In a second loop, the first loop is repeated with the material of the sections varied for each iteration of the first loop. In a third loop, the first two iterations are repeated with the wavelength of the incident beam varied for each iteration of the first loop and each iteration of the second loop. Alternatively, for angle resolved metrology (i.e., metrology where the angle of incidence is varied), in the third loop, the angle of incidence of the incident beam can be varied rather than the wavelength. It should be recognized, however, that the order and number of loops can vary.

In step 906, a hypothetical profile is generated. As described above, a hypothetical profile can be characterized using a set of parameters, which can then be varied to generate the set of hypothetical profiles.

In step 908, the hypothetical profile is divided into sections. In step 910, for each section, a system of differential equations are generated. In step 912, the previously calculated and stored eigensolution that corresponds to the section are retrieved. In step 914, the system of differential equations are solved using the retrieved eigensolution for the section.

In step 916, if the last section has not been reached, steps 910 to 914 are repeated for the remaining sections of the hypothetical profile. If the last section has been reached, in step 918, the solutions for the sections of the hypothetical profiles are coupled to arrive at a solution for the hypothetical profile. In step 920, this solution is then stored as the simulated diffraction signal for the hypothetical profile.

In step 922, if a simulated diffraction signal for another hypothetical profile is to be generated, steps 908 to 920 are repeated. If the last hypothetical profile has been reached, the process is stopped.

In one exemplary embodiment in which a library-based process is used to determine the profile of a structure, a library of hypothetical profiles and corresponding simulated diffraction signals are generated and stored for varying geometry and/or material as well as varying wavelength or angle of incidence based on the previously generated and stored eigensolutions. In one particular exemplary embodiment, the library of hypothetical profiles and corresponding simulated diffraction signals are generated and stored in the same nesting hierarchy as the previously generated and stored eigensolutions.

In another exemplary embodiment in which a regression-based process is used to determine the profile of a structure, one or more simulated diffraction signals are generated based on the previously generated and stored eigensolutions.

6. Trapezoids

As described above, calculating and storing the eigensolutions in advance of generating one or more simulated diffraction signals can reduce the computation time for generating the one or more simulated diffraction signals. In one exemplary embodiment, the computation time for generating one or more simulated diffraction signals is further reduced by generating intermediate calculations (hereafter referred to as "diffraction calculations") for a plurality of blocks of sections (hereafter referred to as "hypothetical layers").

Figure 10:
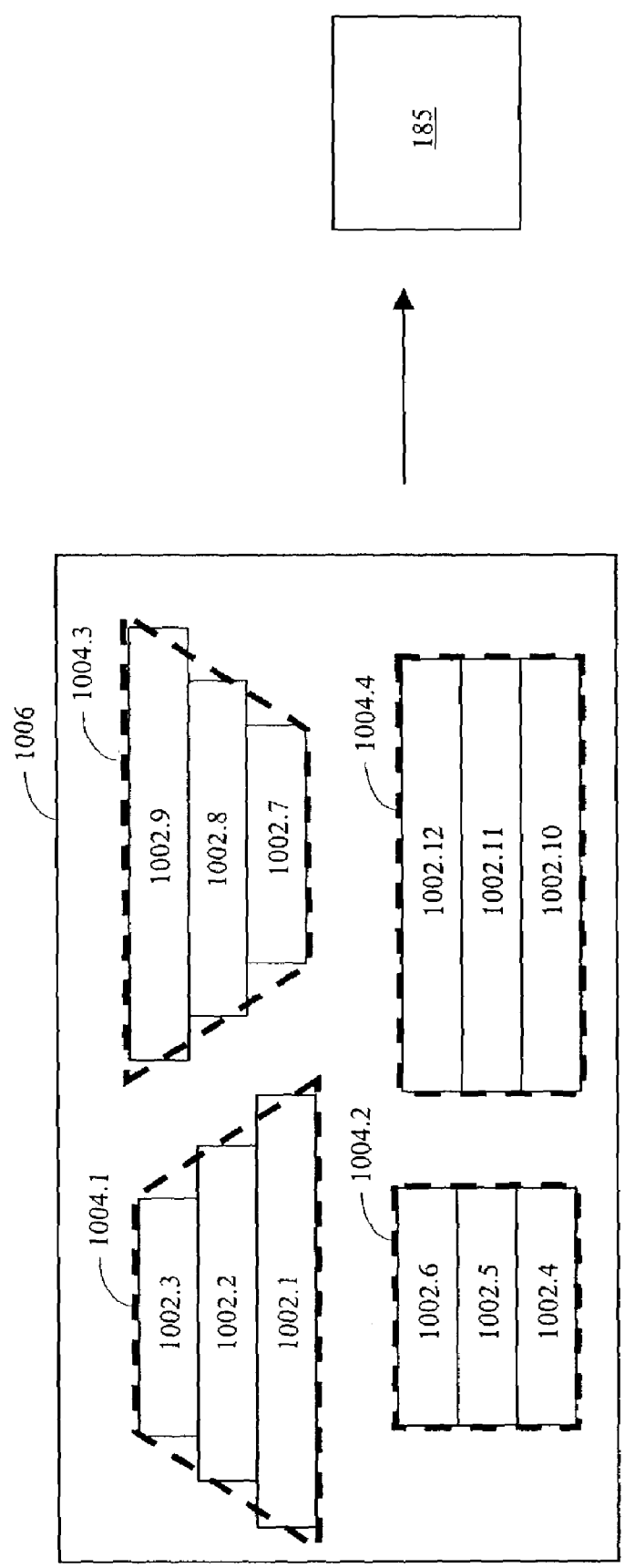
FIG. 10 depicts an exemplary cache of blocks of hypothetical layers and a library.

For example, with reference to FIG. 10, a plurality of hypothetical layers 1002 (e.g., hypothetical layer 1002.1-1002.12) can be grouped together as a block of hypothetical layers 1004 (e.g., block of hypothetical layers 1004.1-1004.4). Each hypothetical layer 1002 (i.e., a section) characterizes a layer (i.e., a portion) of a hypothetical profile.

In the present example, hypothetical layers 1002.1, 1002.2, and 1002.3 are depicted as being grouped together to form block of hypothetical layers 1004.1. Hypothetical layers 1002.4, 1002.5, and 1002.6 are depicted as being grouped together to form block of hypothetical layers 1004.2. Hypothetical layers 1002.7, 1002.8, and 1002.9 are depicted as being grouped together to form block of hypothetical layers 1004.3. Hypothetical layers 1002.10, 1002.11, and 1002.12 are depicted as being grouped together to form block of hypothetical layers 1004.4. In this manner, a number of blocks of hypothetical layers 1004 of various sizes and shapes can be generated. Although blocks of hypothetical layers 1004 are depicted in FIG. 10 as including three hypothetical layers 1002, it should be recognized that they can include any number of hypothetical layers 1002.

Diffraction calculations are generated for each hypothetical layer 1002 within a block of hypothetical layers 1004. Diffraction calculations for each block of hypothetical layers 1004 are then generated by aggregating the diffraction calculations for each hypothetical layer 1002 within each block of hypothetical layers 1004.

Figure 11:
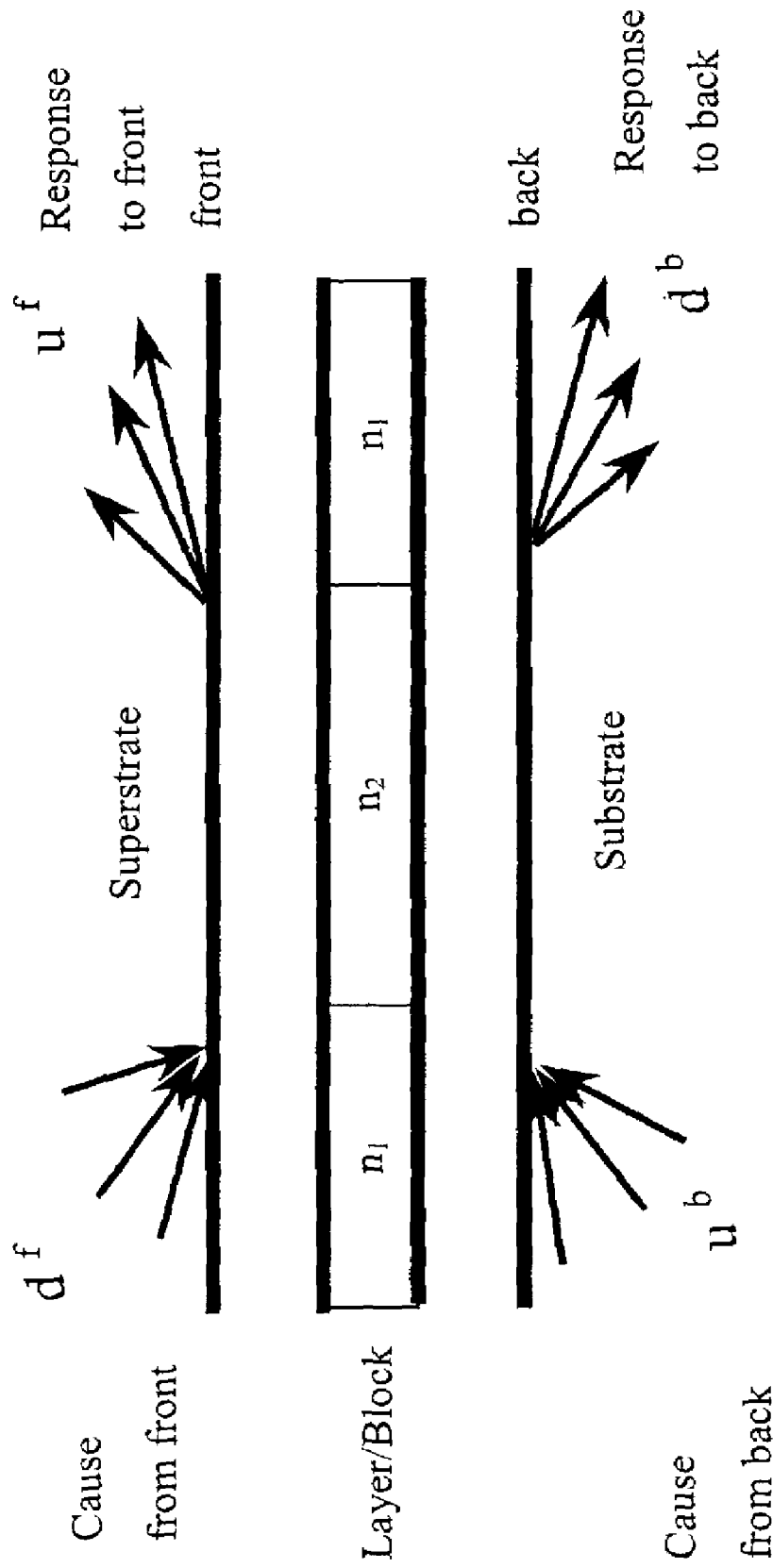
FIG. 11 depicts cause and response fields of the front and back of an exemplary layer or block of layers.

More specifically, in one exemplary embodiment, the results of the diffraction calculations are scattering matrices. With reference to FIG. 11, a scattering matrix S connects the cause to the response fields of the front and back of a layer or block of layers. The scattering matrix has 4 sub-matrices (i.e., reflection matrix $r^f$ and the transmission matrix $t^f$ at front side excitation as well as the reflection matrix $r^b$ and the transmission matrix $t^b$ at back side excitation):

$$\begin{pmatrix} u^f \\ d^b \end{pmatrix} = S \cdot \begin{pmatrix} d^f \\ u^b \end{pmatrix} \quad S = \begin{pmatrix} r^f & t^b \\ t^f & r^b \end{pmatrix}$$

The tangential electromagnetic field components can be obtained from the up- and down-waves by means of the so-called W-matrix.

With reference again to FIG. 10, the diffraction calculations and the blocks of hypothetical layers 1004 are then stored. More particularly, in one exemplary embodiment, pairs of diffraction calculations and blocks of hypothetical layers 1004 are stored in a cache 1006.

For example, for block of hypothetical layers 1004.1, diffraction calculations are generated for hypothetical layers 1002.1, 1002.2, and 1002.3. A diffraction calculation for block of hypothetical layers 1004.1 is then generated by aggregating diffraction calculations for hypothetical layers 1002.1, 1002.2, and 1002.3. Block of hypothetical layers 1004.1 and the diffraction calculations associated with block of hypothetical layers 1004.1 are then stored in cache 1006. In a similar manner, diffraction calculations for blocks of hypothetical layers 1004.2, 1004.3, and 1004.4 are generated and stored in cache 1006.

Although four blocks of hypothetical layers 1004 are depicted and described as being generated and stored in cache 1006, it should be recognized that any number of blocks of hypothetical layers 1004 of various shapes and configurations can be generated and stored in cache 1006. Indeed, in use, cache 1006 may contain tens and hundreds of thousands of blocks of hypothetical layers 1004 and diffraction calculations.

Additionally, although FIG. 10 depicts blocks of hypothetical layers 1004 being stored in cache 1006 in a graphical format, blocks of hypothetical layers 1004 can be stored in various formats. For example, blocks of hypothetical layers 1004 can be stored using parameters that define their shapes.

The stored blocks of hypothetical layers 1004 can then be used to generate one or more simulated diffraction signals for one or more hypothetical profiles. More specifically, one or more blocks of hypothetical layers 1004 can be used to characterize a hypothetical profile, then the corresponding diffraction calculations of the one or more blocks of hypothetical layers 1004 can be used to generate the simulated diffraction signal for the hypothetical profile.

In some applications, one block of hypothetical layers 1004 can be used to characterize a hypothetical profile. For example, with reference to FIG. 12A, assume for the sake of this example that a simulated diffraction signal is to be generated for hypothetical profile 1200A. As described above, a block of hypothetical layers 1004 from cache 1006 is selected that characterizes hypothetical profile 1200A. The appropriate block of hypothetical layers 1004 can be selected using an error minimization algorithm, such as a sum-of-squares algorithm.

As depicted in FIG. 12A, in this example, block of hypothetical layers 1004.1 is selected from cache 1006. The diffraction calculation associated with block of hypothetical layers 1004.1 is then retrieved from cache 1006. Boundary conditions are then applied to generate the simulated diffraction signal for hypothetical profile 1200A.

As described above, the parameters that define hypothetical profile 1200A can be varied to define another hypothetical profile. In this example, with reference to FIG. 12B, assume that the parameters are varied to define hypothetical profile 1200B.

Figure 12B:
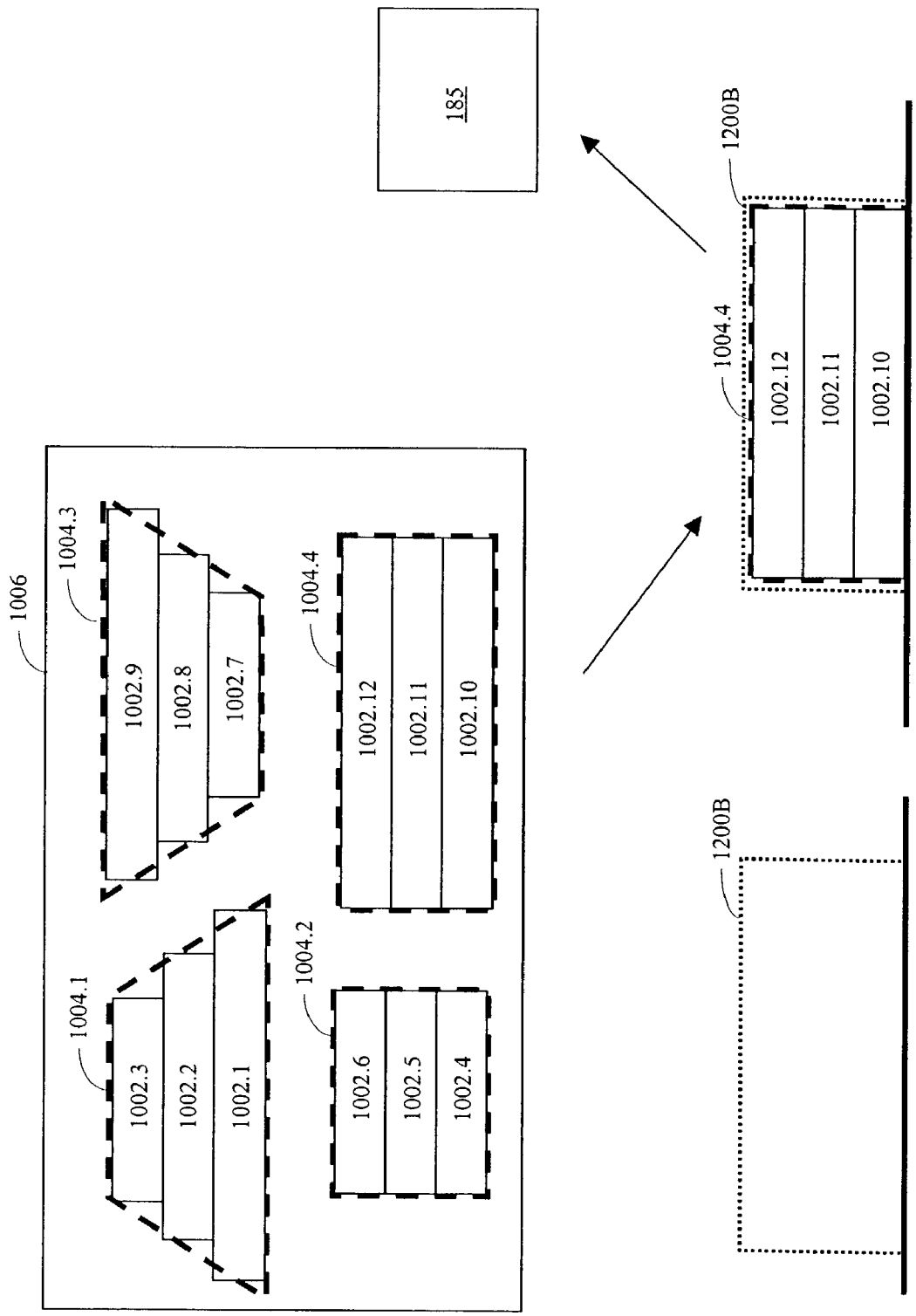

As depicted in FIG. 12B, block of hypothetical layers 1004.4 is selected from cache 1006. The diffraction calculation associated with block of hypothetical layers 1004.4 is then retrieved from cache 1006. Boundary conditions are then applied to generate the simulated diffraction signal for hypothetical profile 1200B.

Figure 13A:
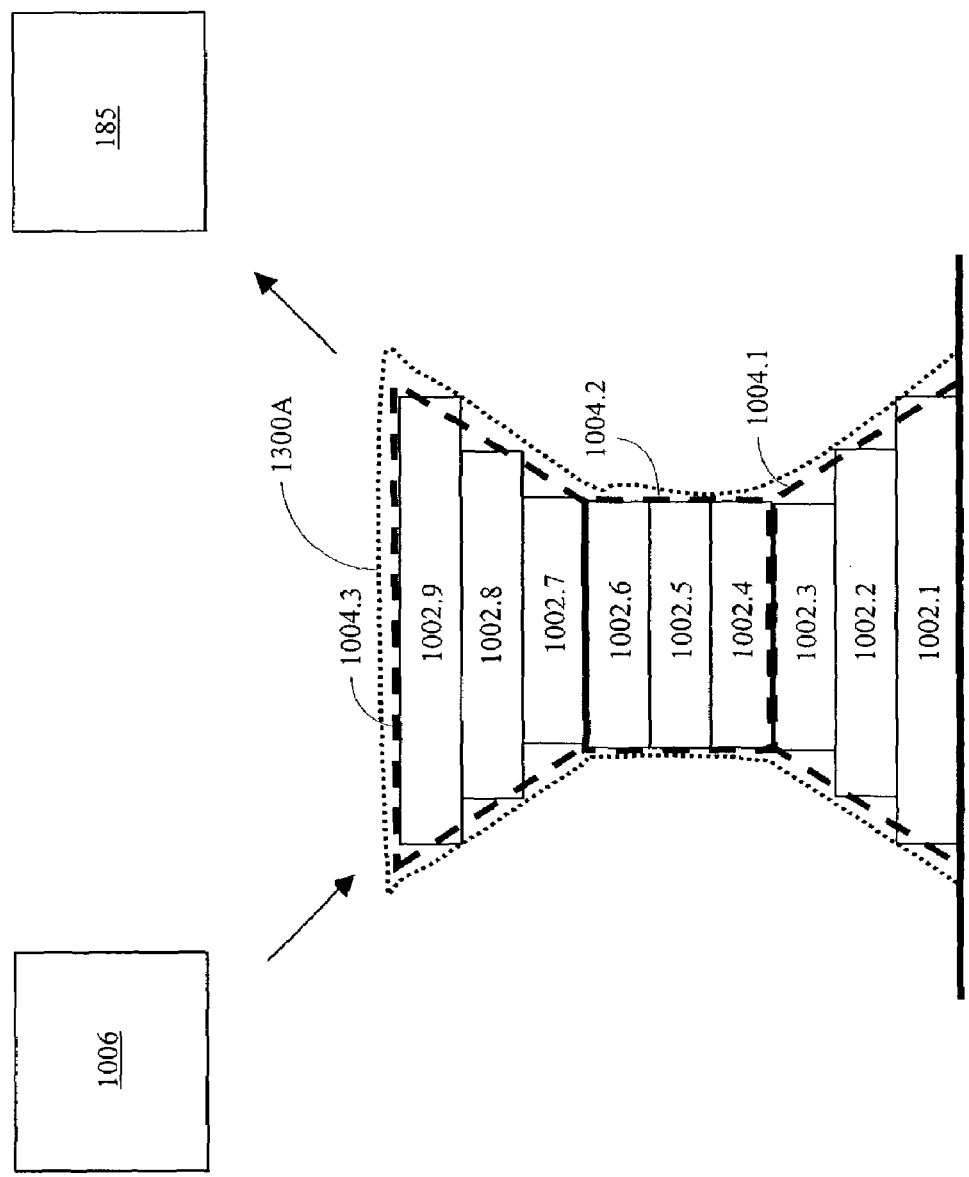

In some applications, multiple blocks of hypothetical layers 1004 can be used to characterize a hypothetical profile. For example, with reference to FIG. 13A, profile 1300A can be characterized by blocks of hypothetical layers 1004.1, 1004.2, and 1004.3. In the present embodiment, an error minimization algorithm can be utilized to determine the appropriate blocks of hypothetical layers 1004 to use in characterizing profile 1300A.

In the present example, for profile 1300A, the diffraction calculations associated with blocks of hypothetical layers 1004.1, 1004.2, and 1004.3 are retrieved from cache 1006. Boundary conditions are then applied to generate the simulated diffraction signal for profile 1300A. More particularly, the boundary conditions at the top and bottom of profile 1300A are applied.

As described above, the parameters that define hypothetical profile 1300A can be varied to define another profile. In this example, with reference to FIG. 13B, assume that the parameters are varied to define hypothetical profile 1300B.

As depicted in FIG. 13B, hypothetical profile 1300B can be characterized by blocks of hypothetical layers 1004.1, 1004.3, and 1004.4. As such, the diffraction calculations associated with blocks of hypothetical layers 1004.1, 1004.3, and 1004.4 are retrieved from cache 1006. Boundary conditions are then applied to generate the simulated diffraction signal for hypothetical profile 1300B.

In some applications, a hypothetical profile can include multiple materials. For example, with reference to FIG. 14A, assume that hypothetical profile 1400 is used to characterize an actual profile of a grating periodic formed from two materials. More particularly, as depicted in FIG. 14A, hypothetical profile 1400 includes a first layer 1402 and a second layer 1404. In the present example, assume that first layer 1402 represents an oxide layer of the actual profile, and second layer 1404 represents a metal layer of the actual profile. Note that hypothetical profile 1400 can include any number of layers to represent layers of any number of materials in an actual profile.

Figure 14B:
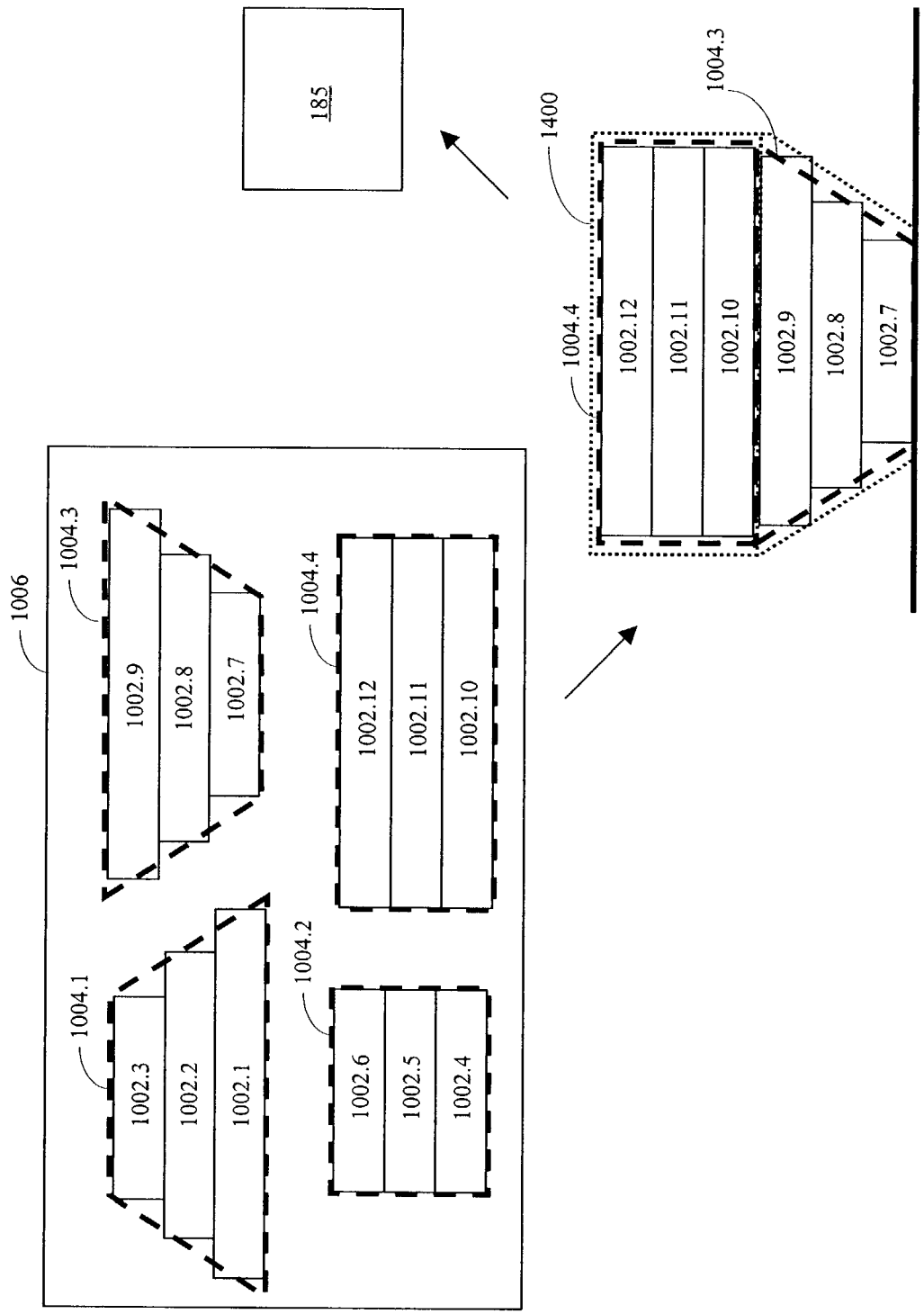

With reference to FIG. 14B, in the present example, assume that cache 1006 includes blocks of hypothetical layers 1004 of various materials as well as various shapes. For example, assume that blocks of hypothetical profiles 1004.1 and 1004.3 represent oxide layers, and hypothetical profiles 1004.2 and 1004.4 represent metal layers. As such, as depicted in FIG. 14B, profile 1400 can be characterized by blocks of hypothetical layers 1004.3 and 1004.4 from cache 1006. Boundary conditions are then applied to generate the simulated diffraction signal for profile 1400.

Thus far, hypothetical layers 1002 and blocks of hypothetical layers 1004 have been depicted as having rectangular and trapezoidal shapes, respectively. As noted earlier, the diffraction calculation for a hypothetical layer 1002 depends on its width but not on its height. However, the diffraction calculation for a block of hypothetical layers 1004 depends on its height as well as its width. Therefore, the blocks of hypothetical layers 1004 stored in cache 1006 are characterized and indexed, in part, by their width and their height. More particularly, when blocks of hypothetical layers 1004 have symmetric-trapezoidal shapes, they can be indexed by their height, bottom width (bottom CD), and top width (top CD). However, as noted earlier, blocks of hypothetical layers 1004 can have various shapes. As such, they can be characterized and indexed using any number of parameters.

Additionally, thus far, a hypothetical profile has been described and depicted as being characterized by a combination of sections (as described in section 3) and a combination of blocks of layers (as described here in section 4). However, it should be noted that a hypothetical profile can be characterizing using a combination of one or more blocks of hypothetical layers and one or more sections.

Furthermore, for the sake of clarity, hypothetical layers and blocks of hypothetical layers have been depicted in two dimensions. It should be noted, however, that for a structure having a profile that varies in two or more dimensions (i.e., two-dimension structure), the hypothetical layers and/or blocks of hypothetical layers can have more complex shapes and parameterizations.

Figure 15:
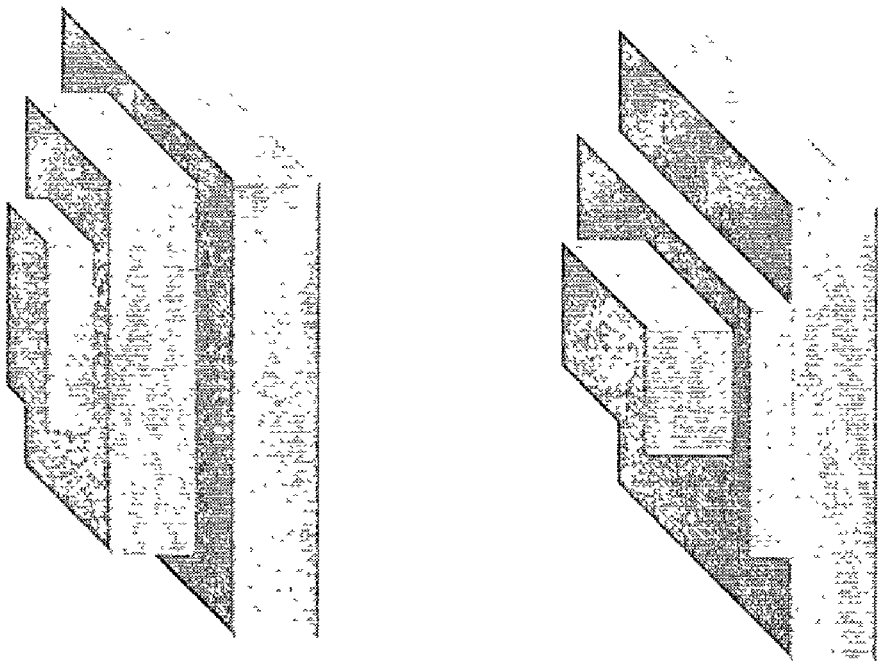
FIG. 15 depicts exemplary blocks of hypothetical layers assembled to correspond to exemplary hypothetical profiles of an exemplary two-dimension structure.
Figure 15:
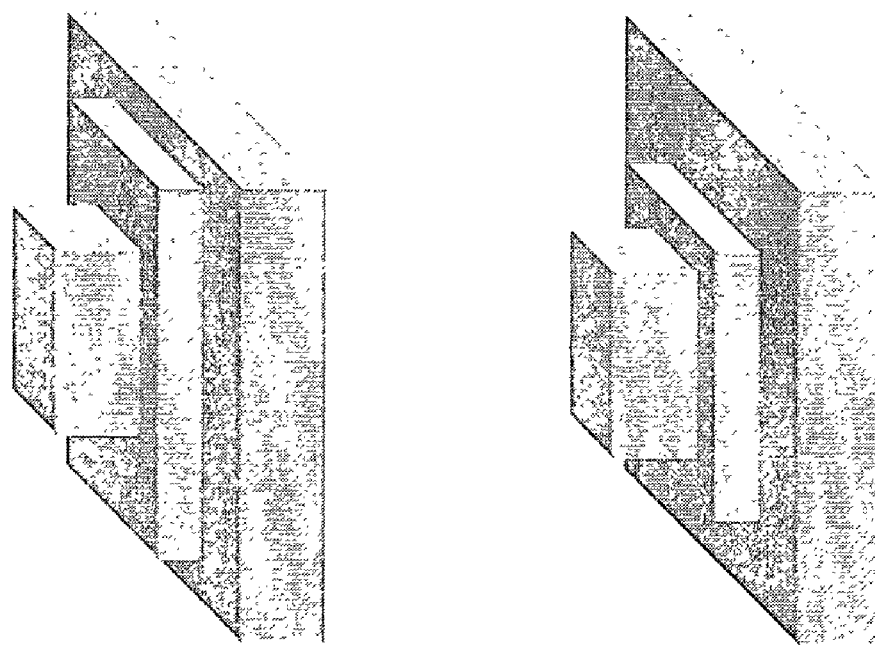

For example, as depicted in FIG. 15, if rectangular blocks of hypothetical layers are used, the blocks can have widths in two dimensions (e.g., a width in a x-direction, a width in a y-direction, which may be orthogonal or not), one or more rounded corners, and the like. Additionally, if elliptical blocks of hypothetical layers are used, such as for contact holes or posts, the elliptical blocks can have diameters (e.g., a diameter in a x-direction, a diameter in a y-direction), a parameter that describes the deviation from an ellipse or a rectangle (e.g., an elliptical exponent that is equal to 2 for an ellipse and increases the more the ellipsoidal cross section shape approaches a rectangle), and the like.

It should be noted, however, that the hypothetical layers and/or blocks of hypothetical layers can have various shapes of varying complexity. For example, the hypothetical layers and/or blocks of hypothetical layers can include combinations of shapes, such as a combination of rectangular shapes.

In one exemplary embodiment in which a library-based process is used to determine the profile of a structure, a library of hypothetical profiles and corresponding simulated diffraction signals are generated and stored for varying geometries and/or material as well as varying wavelength or angle of incidence based on the previously generated and stored blocks of hypothetical layers.

Figure 16:
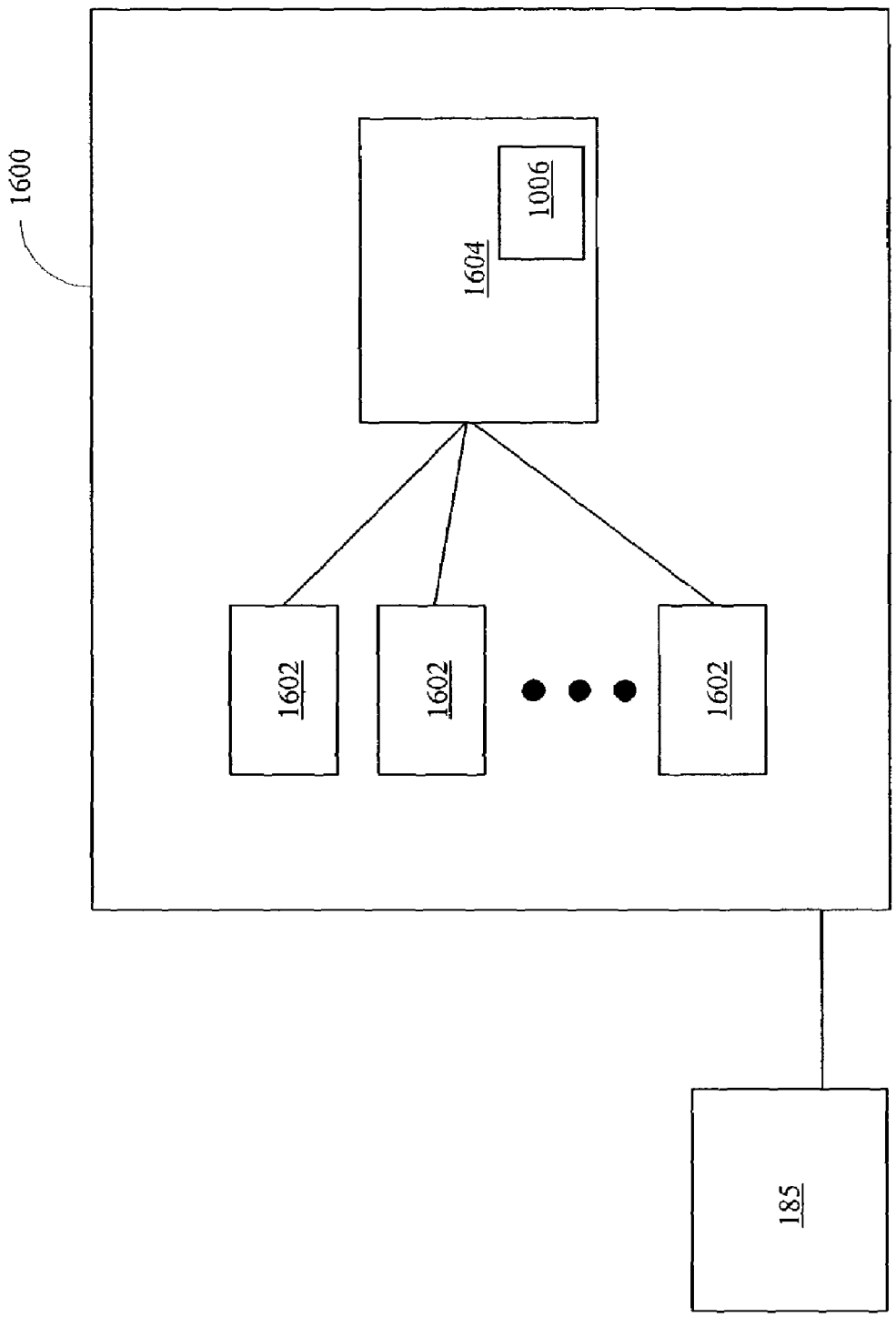
FIG. 16 depicts an exemplary computer system.

With reference to FIG. 16, in one particular exemplary embodiment, library 185 can be generated using a computer system 1600. As noted above and as will be described in greater detail below, the process of generating library 185 can involve performing a large number of complex calculations.

For example, assume that a set of hypothetical profiles is to be generated for a periodic grating that is to have a profile with a bottom CD of 200 nm. Assume that a 10% process variation is expected for the bottom CD of the periodic grating, which means that the bottom CD is expected to vary between about 180 to about 220 nm. Also assume that the top CD is expected to vary between about 160 to about 180 nm. Assume that the nominal thickness (i.e., the height) of the periodic grating is to be about 500 nm, and that a 10% process variation is expected, which means that the height can vary between about 450 to about 550 nm. Now assume that the desired resolution is 1 nm, which means that each parameter of the hypothetical profiles is varied by an increment of 1 nm.

In generating the set of hypothetical profiles, the top CD of the hypothetical profiles is varied between 160 to 180 nm in steps of 1 nm. The bottom CD of the hypothetical profiles is varied between 180 to 220 nm in steps of 1 nm. The thickness/height of the hypothetical profiles is varied between 450 to 550 nm in steps of 1 nm. Thus, in this example, a total of 87,000 hypothetical profiles (i.e., 21 variations of the top CD multiplied by 41 variations of the bottom CD multiplied by 101 variations of the thickness/height).

Now, assume that diffraction calculations are to be generated for each hypothetical profile at 53 different wavelengths. Also assume that each diffraction calculation uses 6 matrices with 9 orders and 8 bytes, which totals 17 kbytes. As such, in this example, to store the diffraction calculations for all of the 87,000 hypothetical profiles at 53 different wavelengths, a total of 78 Gigabytes is needed.

In general, a greater number of simulated diffraction signals are stored in a library for structures having profiles that vary in more than one dimension than for structures having profiles that vary in just one dimension. For example, the computation time for a single solution for a structure having a profile that varies in one dimension (i.e., a one-dimension structure) scales as $M^3$, where M is the number of retained harmonic orders in one direction. In contrast, the computation time for a single solution for a structure having a profile that varies on two dimensions (i.e., a two-dimension structure) scales as $8M^6$. Thus, if a total of ±5 harmonic orders are retained, the difference in computation time for a single solution between the one-dimension structure and the two-dimension structure can increase by a factor of 10648.

As such, computer system 1600 can include multiple processors 1602 configured to perform portions of the computations in parallel. However, computer system 1600 can be configured with a single processor 1602.

Additionally, computer system 1600 can include a memory 1604 configured with a large amount of memory, such as 8 Gigabytes, 16 Gigabytes, 32Gigabytes, and the like, that can be accessed by the multiple processors 1602. It should be recognized, however, computer system 1600 can be configured with any number and size of memories 1604.

Thus, in one exemplary embodiment, simulated diffraction signals for a set of hypothetical profiles to be stored in library 185 can be generated based on the diffraction calculations for blocks of hypothetical layers stored in cache 1006. More particularly, for each hypothetical profile to be stored in library 185, one or more blocks of hypothetical layers that characterize the hypothetical profile are selected from those stored in cache 1006. Boundary conditions are then applied to generate the simulated diffraction signal for the hypothetical profile. The simulated diffraction signal and the hypothetical profile are then stored in library 185. The hypothetical profile can be stored in various formats, such as graphically, using the parameters that define the hypothetical profile, or both.

In one exemplary embodiment, as depicted in FIG. 16, cache 1006 can reside in memory 1604. As such, the blocks of hypothetical layers and hypothetical profiles stored in cache 1006 can be more quickly accessed by computer system 1600, and more particularly processors 1602, than if cache 1006 resided on a hard drive.

Additionally, in one exemplary embodiment, library 185 can reside on various computer-readable storage media. For example, library 185 can reside on a compact disk that is written to by computer system 1600 when library 185 is generated, and read by signal processing module 190 (FIG. 1) when library 185 is used to determine the profile of periodic grating 145 (FIG. 1) on wafer 140 (FIG. 1).

In another exemplary embodiment in which a regression-based process is used to determine the profile of a structure, one or more simulated diffraction signals are generated based on the previously generated and stored blocks of hypothetical layers. The one or more simulated diffraction signals can be generated by one or more processors 1602. Additionally, the blocks of hypothetical layers can be stored in cache 1006. The generated simulated diffraction signals can be stored in library 185.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. Many other variations are also to be considered within the scope of the present invention.

We claim:

1. A method of generating one or more simulated diffraction signals for use in determining the profile of a structure formed on a semiconductor wafer, wherein the profile varies in more than one dimension, the method comprising:
    generating intermediate calculations,
        wherein each intermediate calculation corresponds to a portion of a hypothetical profile of the structure, and
        wherein intermediate calculations are generated for variations in the hypothetical profile in a first dimension and a second dimension;
    storing the generated intermediate calculations; and
    generating one or more simulated diffraction signals for one or more hypothetical profiles for the structure based on the stored intermediate calculations.

2. The method of claim 1, wherein the intermediate calculations are eigenvalues and eigenvectors that are to be used in solving a system of coupled differential equations in a rigorous coupled wave analysis to generate a simulated diffraction signal.

3. The method of claim 2, wherein the hypothetical profile of the structure is divided into a plurality of sections, wherein a set of eigenvalues and eigenvectors correspond to a section having a width and height, and the set of eigenvalues and eigenvectors are sensitive to the width of the section and not sensitive to the height of the section.

4. The method of claim 1, wherein the intermediate calculations are scattering matrices that are to be used in solving a system of coupled differential equations in a rigorous coupled wave analysis to generate a simulated diffraction signal.

5. The method of claim 4, wherein a scattering matrix corresponds to a block of sections, wherein each section corresponds to a portion of a hypothetical profile, wherein each section has a width and height, and wherein the sections within a block of sections have different widths.

6. The method of claim 5, wherein a set of eigenvalues and eigenvectors are generated for each section, and wherein the eigenvalues and eigenvectors are sensitive to the width of a section and not sensitive to the height of a section.

7. The method of claim 1, wherein the intermediate calculations are generated and stored using a nesting hierarchy of parameters.

8. The method of claim 7, wherein the nesting hierarchy includes a first loop, which is nested within a second loop, which is nested within a third loop, wherein a geometry parameter is varied in the first loop, a material parameter is varied in the second loop, and a wavelength or angle of incidence parameter is varied in the third loop.

9. The method of claim 1, wherein the structure is a grating, contact hole, or post.

10. The method of claim 1, wherein the one or more simulated diffraction signals are stored in a library for use in a library-based process for determining the profile of the structure.

11. The method of claim 10, wherein the library-based process comprises:
    obtaining a diffraction signal measured from directing an incident beam at the structure (a measured diffraction signal); and
    comparing the measured diffraction signal to one or more simulated diffraction signals stored in the library to determine the profile of the structure.

12. The method of claim 1, wherein the one or more simulated diffraction signals are generated as part of a regression-based process for determining the profile of the structure.

13. The method of claim 12, wherein the regression-based process comprises:
    obtaining a diffraction signal measured from directing an incident beam at the structure (a measured diffraction signal);
    comparing the measured diffraction signal to a first simulated diffraction signal generated using the stored intermediate calculations; and
    when the measured diffraction signal and the first simulated diffraction signal do not match within a preset criteria:
        generating a second simulated diffraction signal using the stored intermediate calculation; and
        repeating the comparing step using the second simulated diffraction signal.

14. the method of claim 13, wherein the second simulated diffraction signal is generated using an optimization algorithm.

15. A method of generating one or more simulated diffraction signals for use in determining the profile of a structure formed on a semiconductor wafer, wherein the profile varies in more than one dimension, the method comprising:
generating intermediate calculations that are to be used in solving a system of coupled differential equations in a rigorous coupled wave analysis,
wherein each intermediate calculation corresponds to a portion of a hypothetical profile of the structure, and
wherein intermediate calculations are generated for variations in the hypothetical profile in a first dimension and a second dimension;
storing the generated intermediate calculations; and
generating one or more simulated diffraction signals for one or more hypothetical profiles for the structure based on the stored intermediate calculations.

16. The method of claim 15, wherein the intermediate calculations are eigenvalues and eigenvectors, wherein the hypothetical profile of the structure is divided into a plurality of sections, wherein a set of eigenvalues and eigenvectors correspond to a section having a width and height, and the set of eigenvalues and eigenvectors are sensitive to the width of the section and not sensitive to the height of the section.

17. The method of claim 15, wherein the intermediate calculations are scattering matrices, wherein a scattering matrix corresponds to a block of sections, wherein each section corresponds to a portion of a hypothetical profile, wherein each section has a width and height, and wherein the sections within a block of sections have different widths.

18. The method of claim 17, wherein a set of eigenvalues and eigenvectors are generated for each section, and wherein the eigenvalues and eigenvectors are sensitive to the width of a section and not sensitive to the height of a section.

19. The method of claim 15 wherein the intermediate calculations are generated and stored using a nesting hierarchy of parameters.

20. The method of claim 19, wherein the nesting hierarchy includes a first loop, which is nested within a second loop, which is nested within a third loop, wherein a geometry parameter is varied in the first loop, a material parameter is varied in the second loop, and a wavelength or angle of incidence parameter is varied in the third loop.

21. The method of claim 15, wherein the structure is a grating, contact hole, or post.

22. The method of claim 15, wherein the one or more simulated diffraction signals are stored in a library for use in a library-based process for determining the profile of the structure.

23. The method of claim 22, wherein the library-based process comprises:
obtaining a diffraction signal measured from directing an incident beam at the structure (a measured diffraction signal); and
comparing the measured diffraction signal to one or more simulated diffraction signals stored in the library to determine the profile of the structure.

24. The method of claim 15, wherein the one or more simulated diffraction signals are generated as part of a regression-based process for determining the profile of the structure.

25. The method of claim 24, wherein the regression-based process comprises:
obtaining a diffraction signal measured from directing an incident beam at the structure (a measured diffraction signal);
comparing the measured diffraction signal to a first simulated diffraction signal generated using the stored intermediate calculations; and
when the measured diffraction signal and the first simulated diffraction signal do not match within a preset criteria:
generating a second simulated diffraction signal using the stored intermediate calculation; and
repeating the comparing step using the second simulated diffraction signal.

26. The method of claim 25, wherein the second simulated diffraction signal is generated using an optimization algorithm.

27. A method of generating one or more simulated diffraction signals for use in determining the profile of a structure formed on a semiconductor wafer, wherein the profile varies in more than one dimension, the method comprising:
generating intermediate calculations,
wherein each intermediate calculation corresponds to a portion of a hypothetical profile of the structure, and
wherein intermediate calculations are generated for variations in the hypothetical profile in a first dimension and a second dimension;
storing the generated intermediate calculations; and
generating one or more simulated diffraction signals for one or more hypothetical profiles for the structure based on the stored intermediate calculations as part of a library-based process for determining the profile of the structure.

28. The method of claim 27, wherein the library-based process comprises:
obtaining a diffraction signal measured from directing an incident beam at the structure (a measured diffraction signal); and
comparing the measured diffraction signal to one or more simulated diffraction signals stored in a library to determine the profile of the structure.

29. The method of claim 27, wherein the intermediate calculations are eigenvalues and eigenvectors that are to be used in solving a system of coupled differential equations in a rigorous coupled wave analysis to generate a simulated diffraction signal, wherein the hypothetical profile of the structure is divided into a plurality of sections, wherein a set of eigenvalues and eigenvectors correspond to a section having a width and height, and the set of eigenvalues and eigenvectors are sensitive to the width of the section and not sensitive to the height of the section.

30. The method of claim 27, wherein the intermediate calculations are scattering matrices that are to be used in solving a system of coupled differential equations in a rigorous coupled wave analysis to generate a simulated diffraction signal, wherein a scattering matrix corresponds to a block of sections, wherein each section corresponds to a portion of a hypothetical profile, wherein each section has a width and height, and wherein the sections within a block of sections have different widths.

31. The method of claim 30, wherein a set of eigenvalues and eigenvectors are generated for each section, and wherein the eigenvalues and eigenvectors are sensitive to the width of a section and not sensitive to the height of a section.

32. The method of claim 27, wherein the intermediate calculations are generated and stored using a nesting hierarchy of parameters.

33. The method of claim 32, wherein the nesting hierarchy includes a first loop, which is nested within a second loop, which is nested within a third loop, wherein a geometry parameter is varied in the first loop, a material parameter is varied in the second loop, and a wavelength or angle of incidence parameter is varied in the third loop.

34. The method of claim 27, wherein the structure is a grating, contact hole, or post.

35. A method of generating one or more simulated diffraction signals for use in determining the profile of a structure formed on a semiconductor wafer, wherein the profile varies in more than one dimension, the method comprising:
generating intermediate calculations,
wherein each intermediate calculation corresponds to a portion of a hypothetical profile of the structure, and
wherein intermediate calculations are generated for variations in the hypothetical profile in a first dimension and a second dimension;
storing the generated intermediate calculations; and
generating one or more simulated diffraction signals for one or more hypothetical profiles for the structure based on the stored intermediate calculations as part of a regression-based process for determining the profile of the structure.

36. The method of claim 35, wherein the regression-based process comprises:
obtaining a diffraction signal measured from directing an incident beam at the structure (a measured diffraction signal);
comparing the measured diffraction signal to a first simulated diffraction signal generated using the stored intermediate calculations; and
when the measured diffraction signal and the first simulated diffraction signal do not match within a preset criteria:
generating a second simulated diffraction signal using the stored intermediate calculation; and
repeating the comparing step using the second simulated diffraction signal.

37. The method of claim 36, wherein the second simulated diffraction signal is generated using an optimization algorithm.

38. The method of claim 35, wherein the intermediate calculations are eigenvalues and eigenvectors that are to be used in solving a system of coupled differential equations in a rigorous coupled wave analysis to generate a simulated diffraction signal, wherein the hypothetical profile of the structure is divided into a plurality of sections, wherein a set of eigenvalues and eigenvectors correspond to a section having a width and height, and the set of eigenvalues and eigenvectors are sensitive to the width of the section and not sensitive to the height of the section.

39. The method of claim 35, wherein the intermediate calculations are scattering matrices that are to be used in solving a system of coupled differential equations in a rigorous coupled wave analysis to generate a simulated diffraction signal, wherein a scattering matrix corresponds to a block of sections, wherein each section corresponds to a portion of a hypothetical profile, wherein each section has a width and height, and wherein the sections within a block of sections have different widths.

40. The method of claim 39, wherein a set of eigenvalues and eigenvectors are generated for each section, and wherein the eigenvalues and eigenvectors are sensitive to the width of a section and not sensitive to the height of a section.

41. The method of claim 35, wherein the intermediate calculations are generated and stored using a nesting hierarchy of parameters.

42. The method of claim 41, wherein the nesting hierarchy includes a first loop, which is nested within a second loop, which is nested within a third loop, wherein a geometry parameter is varied in the first loop, a material parameter is varied in the second loop, and a wavelength or angle of incidence parameter is varied in the third loop.

43. The method of claim 35, wherein the structure is a grating, contact hole, or post.

* * * * *